United States Patent [19]

Chang et al.

[11] Patent Number: 4,476,338

[45] Date of Patent: Oct. 9, 1984

[54] OLEFINS FROM METHANOL AND/OR DIMETHYL ETHER

[75] Inventors: Clarence D. Chang, Princeton; Cynthia T. W. Chu, Pennington; Patrick D. Perkins, Titusville, all of N.J.; Ernest W. Valyocsik, Yardley, Pa.

[73] Assignee: Mobil Oil Corporation, New York, N.Y.

[21] Appl. No.: 500,519

[22] Filed: Jun. 2, 1983

[51] Int. Cl.³ .............................................. C07C 1/20
[52] U.S. Cl. .................................. 585/322; 585/640
[58] Field of Search ............... 585/408, 469, 640, 639, 585/733, 322

[56] References Cited

U.S. PATENT DOCUMENTS

| | | | |
|---|---|---|---|
| 4,058,576 | 11/1977 | Chang et al. ........................ | 585/322 |
| 4,300,011 | 11/1983 | Rollmann ............................ | 585/467 |
| 4,328,384 | 5/1982 | Daviduk et al. .................... | 585/469 |
| 4,359,595 | 11/1982 | Rollmann ............................ | 585/640 |
| 4,374,295 | 2/1983 | Lee ...................................... | 585/640 |
| 4,387,263 | 6/1983 | Vogt et al. .......................... | 585/640 |
| 4,397,827 | 8/1983 | Chu ..................................... | 423/326 |
| 4,423,274 | 12/1983 | Daviduk et al. .................... | 585/640 |

Primary Examiner—Delbert E. Gantz
Assistant Examiner—A. Pal
Attorney, Agent, or Firm—A. J. McKillop; M. G. Gilman; J. F. Powers, Jr.

[57] ABSTRACT

A process for converting methanol and/or dimethyl ether to olefins at moderate temperature and atmospheric pressure comprising contacting the feed with an alumina crystalline zeolite catalyst designated as ZSM-48. The olefins formed can then be converted to a low-durene gasoline over ZSM-5 type catalysts under conventional aromatizing conditions or to a distillate boiling above the gasoline range.

13 Claims, No Drawings

OLEFINS FROM METHANOL AND/OR DIMETHYL ETHER

BACKGROUND OF THE INVENTION

1. Field of the Invention

This invention is concerned with the manufacture of light olefin hydrocarbons from lower alcohols or their ethers. It is particularly concerned with the catalytic conversion of such alcohols and ethers selectively to a hydrocarbon mixture characterized by a predominance of olefins. This invention further provides a novel method for converting methanol and/or dimethyl ether to low durene-content gasoline or gasoline blending stocks as well as higher boiling distillates and lubes.

2. Description of the Prior Art

A remarkable growth in the production of synthetic fibers, plastics and rubber has taken place in recent decades. This growth, to a very large extent, has been supported and encouraged by an expanding supply of inexpensive petrochemical raw materials such as ethylene, propylene, and other four and five carbon olefins. Side by side with this remarkable devlopment, there has been an increasing demand for alkylate, made by reacting olefins with isobutane, for use as a high octane gasoline component. Environmental factors which limit the lead content of gasoline are likely to aggravate the need for alkylate.

Burgeoning demand for olefins, particularly ethylene, propylene and butenes, has of couse led to periods of shortage, either due to short supply of suitable feedstocks or to limited processing capacities. In any case, it would appear desirable to provide efficient means for converting raw materials other than petroleum to olefins.

In recent years, the patent art has disclosed that methanol and/or dimethyl ether, which may be obtained from coal, natural gas or biomass, can be converted to more complex hydrocarbons, such as olefins and aromatics, by utilizing a novel group of zeolites, exemplified by ZSM-5 zeolites. The $C_2$–$C_4$ olefinic hydrocarbons may be obtained in this catalytic conversion. The reaction is hightly exothermic and the olefins initially formed have a tendency to undergo further reaction to product aromatic hydrocarbons useful in the production of motor gasoline. A large body of this patent art is concerned with various aspects of selectively converting methanol and/or dimethyl ether to light olefins.

The production of olefins from aliphatic ethers by catalytic conversion with an HZSM-5 zeolite catalyst is disclosed in U.S. Pat. No. 3,894,106 of Chang et al. U.S. Pat. No. 4,025,572 of Lago discloses that ethylene selectivity can be improved by diluting ZSM-5 with an inert diluent while a similar result is achieved, according to U.S. Pat. No. 4,025,575 of Chang et al, through use of subatmospheric partial pressure of the feed. Selectivity with ethylene is also improved by employing a ZSM-5 zeolite in large crystal form of at least one micron either alone (U.S. Pat. No. 4,025,571 of Lago) or in combination with added metals (U.S. Pat. No. 4,148,835 of Chang et al). Better selectivity is also obtained by interdispersing amorphous silica within the interior of the crystalline structure of the zeolite catalyst such as disclosed in U.S. Pat. Nos. 4,060,568 and 4,100,219 of Rodewald.

The conversion of methanol and/or dimethyl ether to gasoline is another important area of technology which has the potential of becoming even more important as the supply of crude oil is diminished and/or increased in price. Particularly, an advantageous catalyst which is utilized in the conversion of methanol to gasoline is a special class of crystalline aluminosilicate zeolite catalysts of which HZSM-5 is the most preferred member. There are many patents and publications which describe the conversion of methanol to gasoline over special zeolites, including U.S. Pat. Nos. 3,931,349; 3,969,426; 3,899,544; 3,894,104; 3,940,916; and 3,894,102; the disclosures of which are incorporated by reference.

One particular problem residing in the conversion of methanol to gasoline over ZSM-5 type zeolites is that durene is produced in amounts higher than that expected from $C_{10}$ aromatic equilibrium distributions. Once an aromatic ring is formed in the presence of unreacted methanol, alkylation to tetramethyl benzenes occurs rapidly, but the smaller higher melting durene molecule (1,2,4,5-tetramethyl benzene, melting point 175° F.) diffuses out the ZSM-5 pore much more rapidly than isodurene (1,2,3,5-tetramethyl benzene) or prehnitene (1,2,3,4-tetramethyl benzene). Durene is an undesirable component of gasoline because of its high melting point. Thus, durene has a tendency to crystallize out of solution at temperatures below 175° F. and deposit within the carburetor or intake manifold of an automobile resulting in an unsatisfactory performance. Based on the results of vehicle testing, an upper limit of 4 wt. % durene in the gasoline is considered acceptable for general motor usage.

There have been various proposals advanced in order to control or minimize the amount of durene which is produced in the catalytic conversion of methanol to gasoline. One proposal has suggested the isomerization of the bottoms fraction of a methanol to gasoline process in order to decrease the durene content. Specifically, U.S. Pat. No. 4,304,951 discloses a process for decreasing the durene content of the bottoms fraction obtained from the catalytic conversion of methanol to gasoline comprising contacting the bottoms fraction with hydrogen at elevated temperatures and pressures over a supported hydrogenation metal catalyst for a period of time sufficient to decrease the durene content and enhance the production of distillate.

U.S. Pat. No. 4,025,576 discloses a process for converting methanol and/or dimethyl ether to low durene-content gasoline or gasoline blending stocks by catalytic contact of the feed at subatmospheric partial pressure with ZSM-5 type catalysts. A multi-stage method for producing gasoline from a methanol feed comprises contacting the feed at a subatmospheric inlet partial pressure of the feed with a first stage ZSM-5 type catalyst at a temperature of 600° F. to 900° F. and thereby convert the methanol to a first stage conversion product comprising steam and light olefin hydrocarbons and contacting in a subsequent stage the first stage conversion product with a subsequent ZSM-5 catalyst at temperatures up to about 1290° F. thereby forming a gasoline product containing low durene contents not above about 2 wt. %.

It is further known that the production of durene can be reduced by operating the methanol-to-gasoline conversion reactor at elevated temperatures. For example, a fixed-bed process with a reactor temperature greater than 850° F., a 3.2 WHSV, 300 psig, 4.5 recycle ratio has yielded high gasoline selectivities, e.g., greater than 85% of the hydrocarbons produced including alkylate, with durene levels at less than 3.5 wt. %. However, at these reaction conditions, a high partial pressure of water is formed. The high partial pressure of water combined with the elevated temperature resulted in rapid permanent catalyst deactivation due to steaming. Operating at temperatures less than 800° F., on the other hand, resulted in satisfactory catalyst life but yielded durene concentrations in the gasoline product of greater than 4 wt. %.

It is also known to convert methanol to olefins over ZSM-5 as discussed above and to subsequently convert the olefins over ZSM-5 to higher olefins, an olefinic distillate and/or to hydrocarbons boiling in the lube oil range.

SUMMARY OF THE INVENTION

In accordance with the present invention, a feed comprising one or more compounds, selected from the lower monohydric alcohols with up to four carbon atoms and their simple or mixed ether derivatives, is substantially converted, to a mixture comprising a major fraction of light olefins, by contact with crystaline aluminosilicate zeolite ZSM-48 at moderate temperatures and pressures. It has been found that ZSM48 has a high intrinsic selectivity at high conversion for the production of olefins from lower monohydric alcohols and ether derivatives thereof such as methanol or dimethyl ether. Previously, the olefin selectivities obtained by the process of the present invention have been observed only with ZSM-5 at high temperatures or at subatmospheric partial pressure of feed.

The alcohols may be manufactured from synthesis gas, i.e. a mixture of CO and $H_2$ made from coal or from natural gas, or they may be produced by fermentation, or manufactured from petroleum fractions in excess supply. The olefin hydrocarbons produced may be converted to alkylate or to aromatics and blended with gasoline, or converted to a high boiling distillate or lube, or they may be separated and used as petrochemicals. Thus, in one aspect, the present invention provides a novel means for producing hydrocarbon petrochemicals and fuels from raw materials other than petroleum.

The mixture of olefins produced by this invention can be characterized as a "conjunct mixture" of olefins, i.e. a product composition unrelated to the exact nature of the feed and from which the feed cannot be recognized. Thus, the conversion of this invention clearly differs from classical dehydration wherein the olefin produced bears a simple relation to the alcohol charge.

In another aspect of this invention, the olefins produced in the conversion of feeds comprising methanol and/or dimethyl ether may be converted in a subsequent step to an aromatic gasoline product which contains substantially less than about 2 wt. % durene. This two-stage process to produce low durene content gasoline from methanol and/or dimethyl ether is most effective when operating the first stage so as to substantially completely convert the methanol and/or dimethyl ether. The olefins formed in the first stage by contact of the methanol feed with ZSM-48 are converted to the low-durene gasoline under conventional conversion conditions typically used to convert methanol to gasoline over ZSM-5 type zeolites, but without the previous disadvantage of excessive durene formation.

DETAILED DESCRIPTION OF THE INVENTION

Any composition comprising one or more alcohol or ether compounds that have the structural formula $(C_nH_{2n+1})$—O—$(C_mH_{2m+1})$ wherein n equals 1 to 4 and m equals 0 to 4 may be used as the reactant feed to the process of this invention. Thus, methanol, ethanol, normal propanol, isopropanol, normal butanol, secondary butanol, isobutanol and tertiary butanol may be used either alone or in admixture with one another, or in admixture with simple ethers of the above alcohols such as dimethyl ether. Likewise, mixed ethers derived from these alcohols, such as methyl-ethyl ether, may be used. It will be noted that all of the compounds indicated have the structural formula above described. Preferred reactant feeds are methanol, dimethyl ether and mixtures thereof, and the above-described compositions that contain at least 10% methanol or dimethyl ether by weight. For the purpose of this invention, the feed need not be of greater than ordinary technical purity. It is an attribute of this invention that other oxygenated compounds such as esters and the like that may be present in the feed, will often convert to hydrocarbons along with the alcohols.

It has now been found that crystalline aluminosilicate zeolite catalyst ZSM-48 has a high intrinsic selectivity at high conversion under moderate temperatures and pressures for the production of olefins from an alcohol feed as discussed above. Previously, the olefin selectivities achieved by the present invention have been observed only with ZSM-5 at high temperatures of about 500° C. or subatmospheric partial pressure of alcohol feed or other methods which have involved disadvantageous manipulation of process conditions and/or the catalyst compositions.

Porous zeolite crystal composition of ZSM-48 can be identified, in terms of moles of anhydrous oxides per 100 moles of silica as follows:

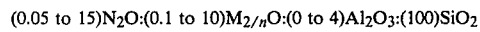

(0.05 to 15)$N_2O$:(0.1 to 10)$M_{2/n}O$:(0 to 4)$Al_2O_3$:(100)$SiO_2$ wherein M is at least one cation having a valence n, N is a mixture of a $C_2$-$C_{12}$, and more preferably of a $C_3$-$C_5$ alkylamine of pKa≧7 and a tetraalkylammonium compound and wherein the composition is characterized by the distinctive x-ray diffraction pattern as shown in Table 1 below.

The original cations can be replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, metals of Groups II and VIII of the Periodic Table and manganese.

The x-ray diffraction pattern of the silico-crystal of the present invention has the significant lines shown in Table 1 and is further characterized by the fact that it exhibits a singlet line within the range of 11.8±0.2 Angstrom units. The novel crystal of this invention does not have more than one x-ray diffraction line at 11.8±0.2 Angstrom units. The presence of only a singlet line at the indicated spacing structurally distinguishes the instant material from closely related materials such as ZSM-12 (U.S. Pat. No. 3,832,449) which has a doublet (two lines) at 11.8±0.2 Angstrom units and high silica ZSM-12 (U.S. Pat. No. 4,104,294) which also exhibits a doublet at 11.8±0.2 Angstrom units.

TABLE 1

| Characteristic Lines of New Silico-Crystal* | |
|---|---|
| d(A) | Relative Intensity ($I/I_o$) |
| 11.8 ± 0.2 | S |
| 10.2 ± 0.2 | W-M |
| 7.2 ± 0.15 | W |
| 4.2 ± 0.08 | VS |
| 3.9 ± 0.08 | VS |
| 3.6 ± 0.06 | W |
| 3.1 ± 0.05 | W |
| 2.85 ± 0.05 | W |

These values were determined by standard techniques. The radiationn was the K-alpha doublet of copper, and a diffractometer equipped with a scintillation counter and a strip chart pen recorder was used. The peak heights, I, and the positions as a function of two times theta, where theta is the Bragg angle, were read from the spectrometer chart. From these, the relative intensities, 100 $I/I_o$, where $I_o$ is the intensity of the strongest line or peak, and d (obs.), the interplanar spacing in A corresponding to the recoded lines, were calculated. In Table 1, the relative intensities are given in terms of the symbols W=weak, VS=very strong, M=medium and W-M=weak to medium (depending on the cationic form). Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

ZSM-48 can be prepared from a reaction mixture containing a source of silica, tetraalkyl ammonium compound, $C_2$-$C_{12}$ alkylamine, an alkali metal oxide, e.g. sodium, with or without a source of alumina, and water, and having a composition, in terms of mole ratios of oxides, falling within the following ranges.

| Reactants | Broad | Preferred |
|---|---|---|
| $Al_2O_3/SiO_2$ | 0 to 0.08 | 0 to 0.02 |
| $Na_2O/SiO_2$ | 0.01 to 1.0 | 0.1 to 0.5 |
| $N_2O/SiO_2$ | 0.005 to 0.5 | 0.005 to 0.25 |
| $OH^-/SiO_2$ | 0 to 0.5 | 0 to 0.2 |
| $H_2O/SiO_2$ | 10 to 200 | 20 to 100 | wherein N is a mixture of a $C_2$-$C_{12}$ alkylamine and tetramethyl ammonium compound, and maintaining the mixture at 80°-200° C. until crystals of the new material are formed.

The molar ratio of $C_2$-$C_{12}$ alkylamine to tetramethyl ammonium compound is not narrowly critical and can range from 1:1 to 10:1. The tetramethyl ammonium compound can include the hydroxide or halide with the chlorine being particularly preferred.

U.S. Ser. No. 303,276, filed Sept. 17, 1981, the entire contents of which are herein incorporated by reference discloses more fully the preparation of ZSM-48.

The conversion of the alcohol feed as described above to olefins in the presence of ZSM-48 proceeds under a relative moderate operating condition, e.g. a temperature of 500° to 1000° F., a pressure of 1 to 150 psia and a space velocity of 0.1 to 100 LHSV. Preferred conditions include 600° to 900° F., 1 to 30 psia and a space velocity of 0.5 to 10 LHSV.

Contact of the feed with the solid catalyst in the process of this invention may be carried out by passing the feed through a bed of the catalyst. The catalyst bed may be any of the fixed, fixed-fluid, or transported bed types. In a fixed or moving bed operation, the average particle size of the catalyst may be as great as 1½" or more, but is generally between about 11/16" and 1¼" in diameter. If a fluid bed is employed, the catalyst must be in finely divided form which can be fluidized by the lifting action of the feed and any diluent vapors. Transport type catalyst beds, such as those in fluid catalytic cracking, may be used.

The effluent from the catalytic conversion step is treated by conventional means to separate the mixture of olefins to whatever extent needed as dictated by the specific intended use of one or more of the olefin products.

The following examples are illustrative of various aspects of the invention without limiting on the scope thereof.

EXAMPLES 1-4

Two ZSM-48 catalysts were synthesized in accordance with the teachings of U.S. Ser. No. 303,276. Thesecatalysts were used in Examples 1 and 2. The ZSM-5 catalysts used in Examples 3 and 4 were prepared in accordance with the disclosure of U.S. Pat. No. 3,702,886.

After synthesis, each catalyst was converted from the as-synthesized form to the hydrogen form by calcination in air (2° F./min to 1000° F.) and held at 1000° F. for 10 hours. The calcined catalysts were exchanged with 1M ammonium nitrate (80° C., 4 hours) and recalcinated as above. The catalysts were then formed into particles of 10-30 mesh.

The respective catalysts were then contacted with methanol or dimethyl ether at the conditions described in Table 2.

The results obtained by the conversion of methanol and dimethyl ether in the presence of ZSM-48 are compared with the product distribution achieved by conversion over ZSM-5 in Table 2. The improved selectivity of ZSM-48 toward olefin production at the moderate operating conditions can be readily seen in Table 2.

TABLE 2

| Example | 1 | 2 | 3 | 4 |
|---|---|---|---|---|
| Catalyst | ZSM-48 | ZSM-48 | ZSM-5 | ZSM-5 |
| $SiO_2/Al_2O_3$ | 113 | 180 | 140 | 220 |
| Feed | MeOH | DME | MeOH | MeOH |
| T, °C. | 370 | 370 | 370 | 370 |
| P, psia | atm | atm | atm | atm |
| LHSV | 1 | 1 | 1 | 1 |
| % Conversion | 99+ | 99+ | 99+ | 96.9 |
| Hydrocarbon Selectivity (wt. %) | | | | |
| Methane | 0.59 | 0.3 | 0.9 | 0.4 |
| Ethane | 0.11 | 0.1 | 0.3 | 0.2 |
| Ethylene | 2.00 | 1.7 | 0.6 | 1.1 |
| Propane | 3.93 | 4.0 | 8.6 | 8.4 |
| Propylene | 12.64 | 10.7 | 1.5 | 3.2 |
| i-Butane | 5.98 | 4.3 | 14.9 | 15.5 |
| n-Butane | 1.05 | 0.9 | 5.7 | 5.7 |
| $C_4$ Olefins | 19.47 | 21.9 | 1.3 | 2.3 |
| i-Pentane | 2.42 | ↑ | ↑ | ↑ |
| n-Pentane | 0.58 | ↑ | ↑ | ↑ |
| $C_5$ Olefins | 12.29 | ↑ | ↑ | ↑ |
| $C_6$ Paraffins | 0.72 | ↑ | ↑ | ↑ |

TABLE 2-continued

| Example | 1 | 2 | 3 | 4 |
|---|---|---|---|---|
| C$_6$ Olefins | 10.06 | 43.7 | 31.4 | 29.6 |
| C$_7$ Olefins | 3.40 | ↓ | ↓ | ↓ |
| C$_7$ Cyclo-olefins | 4.28 | ↓ | ↓ | ↓ |
| C$_8$ Olefins | 0.69 | ↓ | ↓ | ↓ |
| C$_8$ Cyclo-olefins | 5.75 | ↓ | ↓ | ↓ |
| C$_9$ Olefins | 3.54 | ↓ | ↓ | ↓ |
| Toluene | 0.78 | 2.1 | 1.2 | 1.5 |
| Ethylbenzene | 0.33 | ↑ | ↑ | ↑ |
| m,p Xylenes | 1.34 | 2.1 | 7.0 | 6.5 |
| o Xylene | 0.26 | ↓ | ↓ | ↓ |
| C$_9$ Aromatics | 2.48 | ↑ | ↑ | ↑ |
| Durene | 0.29 | ↑ | ↑ | ↑ |
| i-Durene | 0.31 | ↑ | ↑ | ↑ |
| C$_{10}$ Aromatics | 1.44 | 7.2 | 27.5 | 25.6 |
| Pentamethylbenzene | 0.38 | ↓ | ↓ | ↓ |
| C$_{11}$ Aromatics | 1.23 | ↓ | ↓ | ↓ |
| Hexamethylbenzene | 0.1 | ↓ | ↓ | ↓ |
| C$_{12}$+ Aromatics | 1.60 | ↓ | ↓ | ↓ |
| C$_1$-C$_4$ Paraffins | 11.66 | 9.6 | 30.0 | 30.2 |
| C$_2$-C$_4$ Olefins | 34.11 | 34.3 | 3.4 | 6.6 |
| C$_5$+ PON | 43.70 | 43.7 | 31.4 | 29.6 |
| Aromatics | 10.54 | 12.4 | 35.9 | 33.6 |

As shown in the foregoing examples, by-product gasoline components are formed along with desirable olefins. These components include aromatic hydrocarbons and normally isoparaffins which boil from the usual gasoline boiling range of C$_5$+ to 415° F. Thus, if desired, a gasoline boiling range fraction of hydrocarbons may be recovered as by-product when producing olefins by the method of this invention. Such recovery entails simple distillation techniques well known in the art. This gasoline by-product, even though produced from a methanol and/or dimethyl ether feed, is characterized by the durene content of less than about 2 wt.%, which is highly desirable, and it may be used either as high octane gasoline or as a gasoline blending stock. The production of high quality by-product gasoline is an advantageous feature of the present invention.

The method of this invention hereinabove described may be advantageously used as the first stage of a multi-stage method for producing gasoline of unusually low durene content from a feed comprising methanol and/or dimethyl ether.

As previously discussed, it is well known that methanol or dimethyl ether may be converted to gasoline products with a zeolite catalyst typified by the ZSM-5 family. However, the conversions are highly exothermic and are desirably conducted in a fluid bed at pressures above 15 psia to facilitate heat removal. Durene tends to form under such conditions however. Indeed, the reaction performed under appropriate conditions as taught in U.S. Pat. No. 3,894,105, produces high yields of durene.

The conversion of methanol and/or dimethyl ether in the presence of ZSM-48 as hereinabove described produces very little durene even with substantially complete conversion of the alcohol and/or ether. The olefins produced in this first-stage conversion can be aromatized in one or more subsequent stages as described for example in U.S. Pat. No. 3,760,024, issued Sept. 18, 1973, the entire contents of which are incorporated herein by reference. This aromatization reaction may be conducted over any crystalline aluminosilicate zeolite catalyst having a Constraint Index of 1:12 and a silica to alumina ratio of at least 12, particular catalysts in this class being exemplified by the ZSM-5 family in which HZSM-5 and zinc ZSM-5 are particularly preferred. The aromatization of the olefin produced over ZSM-48 is conducted at operating conditions of 600° to 1200° F., a pressure of 15 to 300 psia, and at 0.5 to 10 LHSV. The total effluent from the first stage, which contains the olefins, may be subjected to the aromatization described. It is preferred, however, to separate at least a portion of the steam produced in the first-stage conversion to avoid premature deactivation of the second-stage catalyst, especially if higher temperatures within the described range are used. Other separation of the effluent from the first stage of the reaction may be practiced, such as separating the by-product gasoline, before aromatizing the remainder of the hydrocarbon stream which contains the light olefins. Depending upon the concentration of aromatic hydrocarbons desired in the final gasoline or gasoline blending stock, more or less quantity of the paraffins produced in the first stage may be separated and aromatized together with the olefins produced in the first stage. The aromatization step results in the formation of significant amounts of gasoline in addition to the by-product gasoline formed in the first stage. Furthermore, since this gasoline is free of durene, it serves to reduce the total durene content of the combined gasoline produced in the first and second stages of this process. Thus, by the use of the multi-stage method herein described, methanol and/or dimethyl ether are converted to high quality gasoline having less than about 2 wt. % durene, and in some instances, having less than about 1 wt. % durene.

The following examples are for the purpose of illustrating the multi-stage conversion of this invention and are not to be construed as limiting the invention in any way.

EXAMPLE 5

The product of Example 1, Table 2 was reacted over HZSM-5 at 1000° F., 1 WHSV, 1 atm. The following product was obtained:

| | wt. % of Charge |
|---|---|
| Hydrogen | 1.3 |
| Methane | 7.2 |
| Ethane | 8.2 |
| Ethylene | 2.6 |
| Propane | 23.7 |
| Butanes | 1.5 |
| C$_3$-C$_4$ Olefins | 3.4 |
| C$_5$ + Non-aromatics | 0.2 |
| Benzene | 10.5 |
| Toluene | 20.9 |
| C$_8$ Aromatics | 12.4 |
| C$_9$ Aromatics | 2.6 |
| C$_{10}$ + Mono-Nuclear Aromatics | 0.6 |
| Total Dicyclics | 4.2 |
| Material Balance | 99.3 |

The olefins produced fom the conversion of methanol and/or dimethyl ether over ZSM-48 can also be converted to a higher boiling distillate than gasoline by passing the olefins over a ZSM-5 type zeolite catalyst. Thus, a fuel oil or lube can be formed by passing the olefin product over the ZSM-5 catalyst at a temperature of from about 300°-600° F., a pressure of from about 100-1000 psig and at a space velocity ranging from about 0.1 to 10 WHSV. Such a process is disclosed in U.S. Pat. No. 4,227,992 which is herein incorporated by reference.

The following Example is illustrative.

EXAMPLE 6

The product of Example 1, Table 2 was reacted over HZSM-5 at 478° F., 0.5 WHSV, 1500 psig. The following product was obtained.

|  | wt. % of Charge |
| --- | --- |
| $C_1 + C_2$ | <0.1 |
| $C_3$ | 1.0 |
| $C_4$ | 3.7 |
| $C_5$ | 4.6 |
| $C_6 - 330°$ F. | 11.8 |
| 330-650° F. | 54.4 |
| 650° F. + | 24.5 |
|  | 100.0 |

What is claimed is:

1. A method for converting a feed to light olefins, said feed consisting essentially of one or more compounds selected from the group consisting of a lower monohydric alcohol with up to four carbon atoms and their simple and mixed ether derivatives, said method comprising passing said feed over a catalyst contained in a reaction zone at a space velocity of about 1 to about 100 LHSV with the temperature in said reaction zone at about 500° F. to about 1000° F. and a pressure of about 1 psia to about 15 psia, said catalyst comprising crystalline aluminosilicate zeolite ZSM-48, withdrawing from said reaction zone an effluent comprising a hydrocarbon mixture containing said light olefins.

2. The method of claim 1 wherein said feed is passed over said catalyst at a space velocity of about 1 to about 10 LHSV with the temperature in said reaction zone at about 600° F. to about 900° F.

3. The method of claim 1 wherein said feed comprises methanol or a mixture of methanol and dimethyl ether.

4. The method of claim 1 wherein said effluent is treated to separate said light olefins.

5. The method of claim 1 comprising contacting said effluent in a subsequent reaction zone with a subsequent stage zeolite catalyst having a constraint index of 1 to 12 and a silica to alumina ratio of at least 12, said contacting being under aromatizing conditions at an elevated temperature and a pressure of 15 to 300 psia, thereby forming a subsequent stage conversion product comprising gasoline boiling range hydrocarbons.

6. The method of claim 5 wherein the temperature in said subsequent reaction zone is from about 600° F. to about 1200° F.

7. The method of claim 5 including the step of removing gasoline products from said effluent prior to contacting said effluent with said subsequent stage zeolite catalyst.

8. The method of claim 5 including the step of removing steam from said effluent prior to contacting said effluent with said subsequent stage zeolite catalyst.

9. The method of claim 5 wherein said subsequent stage zeolite catalyst is selected from the group consisting of HZSM-5 and ZnZSM-5.

10. The method of claim 5 wherein said feed comprises methanol or a mixture of methanol and dimethyl ether.

11. The method of claim 1 comprising contacting said effluent in a subsequent reaction zone with a subsequent stage zeolite catalyst, said catalyst having a constraint index of 1 to 12 and a silica to alumina mol ratio of at least about 12, said contacting being under conditions of elevated temperatures of from about 300°-600° F. and a pressure of from about 100-1000 psig to from a distillate range hydrocarbon boiling above about 330° F.

12. The method of claim 11 wherein said subsequent stage zeolite catalyst is HZSM-5.

13. The method of claim 11 wherein said feed comprises methanol or a mixture of methanol and dimethyl ether.

* * * * *